(12) United States Patent
Sutradhar et al.

(10) Patent No.: US 7,919,428 B2
(45) Date of Patent: Apr. 5, 2011

(54) METHOD OF MAKING MIXED METAL OXIDE CATALYSTS FOR AMMOXIDATION AND/OR OXIDATION OF LOWER ALKANE HYDROCARBONS

(75) Inventors: Bhagya Chandra Sutradhar, Aurora, IL (US); Thomas L. Szabo, Schaumburg, IL (US); Muin S. Haddad, Naperville, IL (US); Mark A. Toft, Somonauk, IL (US); Christos Paparizos, Willoughby, OH (US); Lina K. Bodiwala, Naperville, IL (US)

(73) Assignee: Ineos USA LLC, Lisle, IL (US)

( * ) Notice: Subject to any disclaimer, the term of this patent is extended or adjusted under 35 U.S.C. 154(b) by 451 days.

(21) Appl. No.: 11/999,332

(22) Filed: Dec. 4, 2007

(65) Prior Publication Data

US 2009/0142254 A1    Jun. 4, 2009

(51) Int. Cl.
*B01J 27/057* (2006.01)
*B01J 23/00* (2006.01)

(52) U.S. Cl. ........ 502/215; 502/305; 502/311; 502/312; 502/321; 502/353

(58) Field of Classification Search .......... 502/215, 502/305, 311, 312, 321, 353
See application file for complete search history.

(56) References Cited

U.S. PATENT DOCUMENTS

| 5,973,186 | A  | * | 10/1999 | Midorikawa et al. | ......... 558/319 |
| 6,036,880 | A  | * | 3/2000  | Komada et al. | .......... 252/183.13 |
| 6,063,728 | A  | * | 5/2000  | Hinago et al. | ................ 502/300 |
| 6,710,011 | B2 | * | 3/2004  | Mamedov et al. | ............ 502/353 |
| 2004/0092768 | A1 | * | 5/2004 | Borgmeier et al. | ........... 562/547 |
| 2008/0248947 | A1 | * | 10/2008 | Zajac et al. | .................... 502/312 |

FOREIGN PATENT DOCUMENTS

WO           09/73171       *  6/2009
* cited by examiner

*Primary Examiner* — Patricia L Hailey
(74) *Attorney, Agent, or Firm* — David P. Yusko; Vik Panchal

(57) ABSTRACT

The present invention comprises a method for preparing a mixed oxide catalyst for use in producing acrylonitrile or methacrylonitrile from propane or isobutene by ammoxidation in a gaseous phase via methods of heating or calcining precursor solid mixture to obtain mixed metal oxide catalyst compositions that exhibit catalytic activity.

25 Claims, 2 Drawing Sheets

Figure 1:
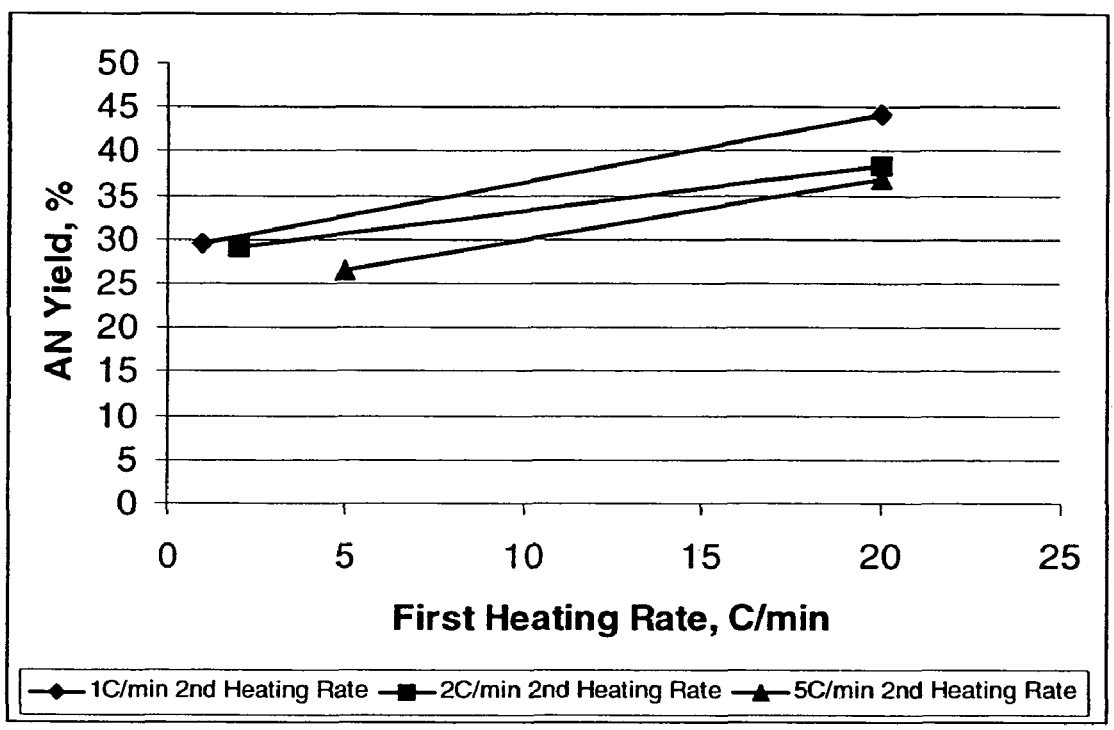

METHOD OF MAKING MIXED METAL OXIDE CATALYSTS FOR AMMOXIDATION AND/OR OXIDATION OF LOWER ALKANE HYDROCARBONS

TECHNICAL FIELD

The present invention relates to method of preparation of solid compositions containing mixed metal oxides that exhibit catalytic activity for ammoxidation or oxidation of lower alkane hydrocarbons to produce an unsaturated mononitrile or acrylic acid in high yield. Mixed metal oxide catalyst compositions of the invention comprise, as component elements, molybdenum (Mo), vanadium (V), niobium (Nb), oxygen (O) and at least one element selected from the group consisting of antimony (Sb) and tellurium (Te).

BACKGROUND OF THE INVENTION

Nitriles such as acrylonitrile and methacrylonitrile have long been industrially produced as important intermediates for the preparation of synthetic fibers, synthetic resins, synthetic rubbers and the like. A major use of acrylonitrile is in the form of fibers. Acrylonitrile-butadiene-styrene terpolymers (ABS) are important thermoplastic structural plastics. Nitrile-type rubbers, first commercialized as the German Buna-N type in 1930, are copolymers of acrylonitrile and a diene, usually butadiene.

The currently practiced commercial processes for the production of nitrites, such as acrylonitrile and methacrylonitrile, subject an alkene, i.e., propylene or isobutene, to reaction in a gas phase with ammonia and oxygen in the presence of a catalyst at a high temperature. Generally, the catalyst formulations employed are proprietary to the catalyst supplier, but the technology is well established. Furthermore, it is known to include additional starting materials, including additional reactants, such as molecular oxygen and/or steam, gas, and inert materials, such as nitrogen and carbon dioxide, along with the hydrocarbon starting material.

In view of the relative abundance of lower alkanes relative to corresponding alkenes, resulting in price differences particularly between propane and propylene or between isobutane and isobutene, attention has been drawn to developing improved catalysts for producing nitriles from these, less expensive, lower alkanes. Propane or isobutane is used as starting material in an ammoxidation reaction with ammonia and oxygen in a gas phase in the presence of a catalyst.

Catalysts containing molybdenum, vanadium, antimony and niobium which have been shown to be effective for conversion of propane to acrylonitrile and isobutane to methacrylonitrile (via an ammoxidation reaction) and methods of preparation of said catalysts are described in numerous publications, patents and patent applications. See, for example, U.S. Pat. No. 5,750,760 to Ushikubo et al., U.S. Pat. No. 6,036,880 to Komada et al., U.S. Pat. No. 6,143,916 to Hinago et al., and U.S. Pat. No. 6,514,902 to Inoue et al.

Oxide catalysts containing molybdenum, tellurium, vanadium, and niobium and methods of preparation of said catalysts are described in U.S. Pat. No. 5,049,692, U.S. Pat. No. 5,231,214, U.S. Pat. No. 5,281,745, U.S. Pat. No. 5,380,933, and U.S. Pat. No. 5,422,328. Further, oxide catalysts containing molybdenum, vanadium, niobium, and antimony are described, for example, U.S. Pat. No. 4,760,159, U.S. Pat. No. 4,797,381, and U.S. Pat. No. 7,087,551.

The methods of preparation of said catalysts can generally be divided in two categories, namely, hydrothermal and non-hydrothermal. In the so-called hydrothermal route generally an aqueous mixture of ingredients is treated at an elevated temperature (e.g., 150-250° C.) and elevated pressure (e.g., 200-300 psig) to presumably form mixed oxide catalytic phases. In the non-hydrothermal route generally an aqueous mixture of ingredients is treated at a temperature generally less than 100° C. at ambient pressure followed by drying to prepare a catalyst precursor. The catalyst precursor is heat treated or calcined to form the catalytic phases. For example, some prior art discloses a method of non-hydrothermal preparation of a catalyst composition with molybdenum, vanadium, antimony and niobium as component metals while other prior art discloses a non-hydrothermal method of preparation of a catalyst composition with molybdenum, vanadium, antimony, niobium and cerium as component metals. The teaching include that calcination is conducted under calcination conditions wherein the heating temperature of a dried catalyst precursor is continuously or intermittently elevated from a temperature which is less than 400° C. to a temperature which is in the range of from 550 to 700° C. At least a part of the calcination is performed in an atmosphere of a flowing gas, which can further comprise a flowing inert gas (e.g. such as noble gases, and the like). The flowing gas is supplied at a flow rate not less than 50 N liters/hour/kg of the dried catalyst precursor. It is also taught that the calcination may comprise a preliminary calcination and a final calcination, wherein the preliminary calcination is performed at a temperature in the range of from 250 to 400° C. and the final calcination is performed at a temperature in the range of from 550 to 700° C. Prior art teachings provide calcination in the presence of flowing gas at a temperature in the range of 500 to 800° C. following a pre-calcination in the presence of air at a temperature in the range of 200 to 400° C. These calcination processes involve long calcination time and multiple calcination units. Also, small variations in calcination conditions (e.g. temperature) appeared to significantly impart the performance of the catalyst. For commercial application it would be desirable to have a shorter calcination time and fewer calcination units.

It is an object of the invention to overcome one or more of the problems described above.

SUMMARY OF THE INVENTION

In broad aspect, the present invention relates to method of making mixed metal oxide catalyst compositions that exhibit an ability to facilitate ammoxidation or oxidation of a saturated hydrocarbon to the corresponding unsaturated nitrile or unsaturated carboxylic acid in high yield, and processes using these catalysts for economical conversions of lower alkane hydrocarbons. Generally, the mixed metal oxide catalyst compositions of the invention comprise, as component elements, molybdenum (Mo), vanadium (V), niobium (Nb) and at least one active element selected from the group consisting of antimony (Sb) and tellurium (Te). In an embodiment compositions of this invention comprise oxides of molybdenum, vanadium, antimony, niobium, at least one element selected from the group consisting of lithium, titanium, tin, germanium, zirconium, hafnium, and optionally at least one lanthanide selected from the group consisting of lanthanum, praseodymium, neodymium, samarium, europium, gadolinium, dysprosium, holmium, erbium, thulium, ytterbium and lutetium. In an embodiment compositions of this invention comprise oxides of molybdenum, vanadium, tellurium, niobium, at least one element selected from the group consisting of lithium, titanium, tin, germanium, zirconium, hafnium, and optionally at least one lanthanide selected from the group consisting of lanthanum, praseodymium, neodymium, samarium, europium, gadolinium, dysprosium, holmium, erbium, thulium, ytterbium and lutetium.

In particular, the present invention discloses a method of heat treating or calcining a solid precursor to the above mixed metal oxide catalyst compositions.

The present invention, therefore, discloses a method of preparation of a mixed oxide catalyst comprising as component elements, molybdenum (Mo), vanadium (V) niobium (Nb), oxygen (O) and at least one element selected from the group consisting of antimony (Sb) and tellurium (Te), that can be used for ammoxidation or oxidation of propane and iso-butane in the gaseous phase, said method comprising elevating in the presence of flowing gas a precursor solid mixture comprising compounds of molybdenum (Mo), vanadium (V), niobium (Nb), oxygen (O) and at least one element selected from the group consisting of antimony (Sb) and tellurium (Te) at a first heating rate greater than about 15° C./min at least once until the solid mixture attains a temperature of not greater than 400° C.

In one embodiment of this invention the precursor solid mixture is maintained at a constant temperature in the range of about 300 to about 400° C. for a period of about 1 to about 4 hours.

The present invention also discloses a method of preparation of a mixed oxide catalyst comprising as component elements, molybdenum (Mo), vanadium (V), niobium (Nb), oxygen (O) and at least one element selected from the group consisting of antimony (Sb) and tellurium (Te), that can be used for ammoxidation or oxidation of propane and iso-butane in the gaseous phase, said method comprising introducing in the presence of flowing gas a precursor solid mixture comprising compounds of molybdenum (Mo), vanadium (V), niobium (Nb), oxygen (O) and at least one element selected from the group consisting of antimony (Sb) and tellurium (Te) into a hot zone maintained at a hot zone temperature greater than about 100° C., greater than about 200° C., greater than about 300° C., or greater than about 400° C.

For a more complete understanding of the present invention, reference should be made to the embodiments described in greater detail below and by way of examples of the invention.

FIGURE BRIEF DESCRIPTION

FIG. 1 schematically illustrates that the present process provides improved acrylonitrile yield as the first heating rate increases according to an embodiment of the present invention.

Figure 2:
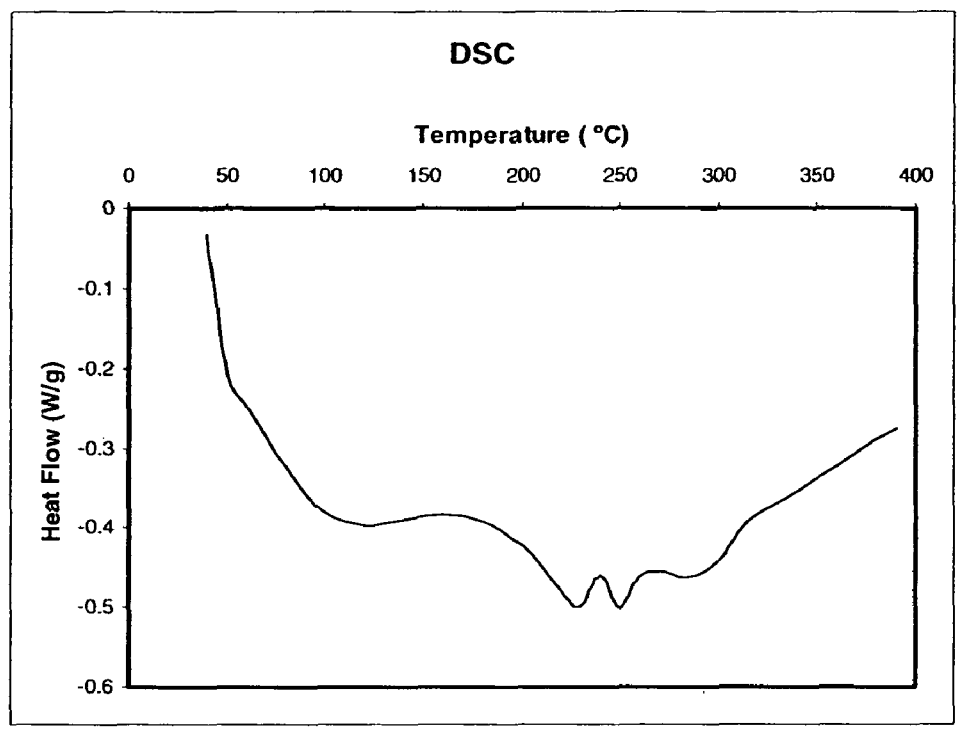

FIG. 2 schematically illustrates DSC temperature points comprising reactions of the present process.

Figure 3:
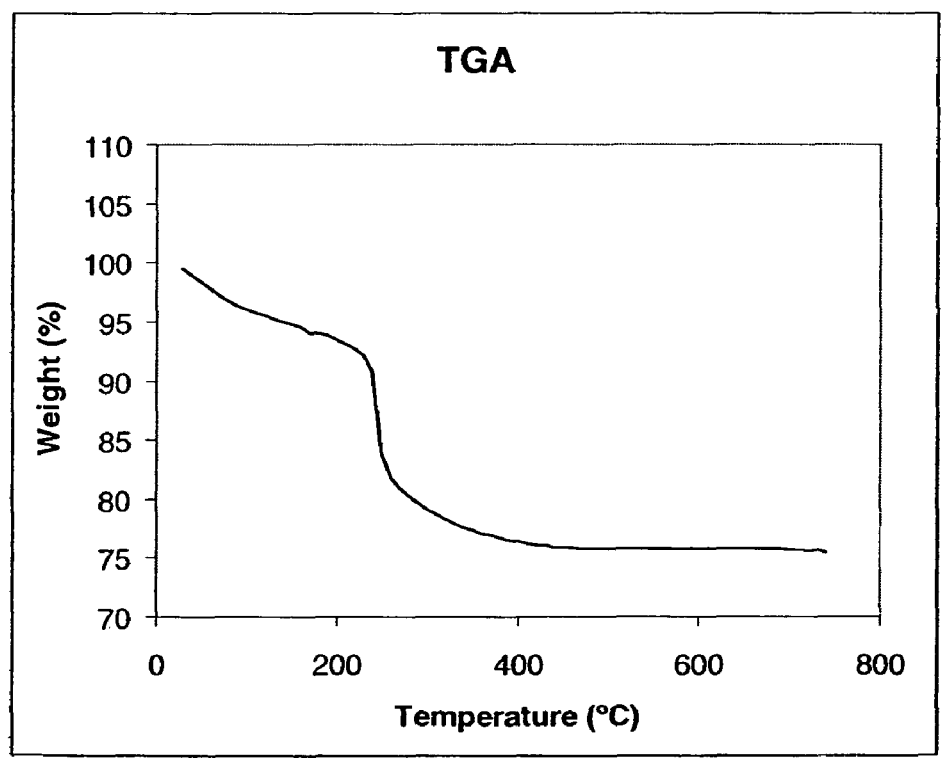

FIG. 3 schematically illustrates TGA temperature points comprising reactions of the present process.

GENERAL DESCRIPTION

The present invention comprises a method for preparing a mixed oxide catalyst for use in producing acrylonitrile or methacrylonitrile from propane or isobutene by ammoxidation in a gaseous phase comprising the elements molybdenum (Mo), vanadium (V), niobium (Nb), oxygen (O) and at least one element selected from the group consisting of antimony (Sb) and tellurium (Te), further comprising heating precursor solid mixture, comprising compounds of molybdenum (Mo), vanadium (V) niobium (Nb), oxygen (O) and at least one element selected from the group consisting of antimony (Sb) and tellurium (Te), contacting with flowing gas at a first heating rate greater than about 15° C./min until the precursor solid mixture attains a precalcination temperature of not greater than 400° C.

An embodiment of the mixed oxide catalyst wherein the precursor solid mixture comprises heating at a second heating rate greater than about 0.5° C./min until the precursor solid mixture attains a temperature of about 590-680° C. The present invention can comprise a second heating rate greater than about 1° C./min, 2° C./min, or 5° C./min. Also, the second heating rate is performed at an atmosphere substantially free of oxygen. Furthermore, the precursor solid mixture comprises holding at a temperature of about 590-680° C. for about two (2) hours.

As an embodiment mixed oxide catalyst comprises the elements molybdenum (Mo), vanadium (V), niobium (Nb), antimony (Sb), and oxygen (O). Also, as an embodiment mixed oxide catalyst comprises the elements molybdenum (Mo), vanadium (V), niobium (Nb), tellurium (Te), and oxygen (O). In an another embodiment, the mixed oxide catalyst comprises the elements molybdenum (Mo), vanadium (V), niobium (Nb), antimony (Sb), tellurium (Te), and oxygen (O).

Further, as an embodiment the precursor solid mixture of the present invention comprises the elements molybdenum (Mo), vanadium (V), niobium (Nb), antimony (Sb), and oxygen (O). As an embodiment the precursor solid mixture comprises the elements molybdenum (Mo), vanadium (V), niobium (Nb) tellurium (Te) and oxygen (O). In an another embodiment, the precursor solid mixture comprises the elements molybdenum (Mo), vanadium (V), niobium (Nb), antimony (Sb), tellurium (Te), and oxygen (O).

The present invention contemplates using inert gas. The inert gas can comprise a noble gas. The gas can comprise nitrogen. The gas can comprise selection from air, steam, super heated steam, carbon monoxide, and carbon dioxide. The flowing gas can comprise a rate of about 1.33-1.67 cm³ μg/min. The gas flow rate depends on the reactor size. In an embodiment the first heating rate greater than about 20° C./min.

In an embodiment the precursor solid comprises the empirical formula:

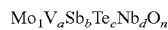

$$Mo_1V_aSb_bTe_cNb_dO_n$$

wherein $0.1 \leq a \leq 1.0$, $0 \leq b \leq 1.0$, $0 \leq c \leq 1.0$, $0.001 \leq d \leq 0.25$; n is the number of oxygen atoms required to satisfy valance requirements of all other elements present in the precursor solid with the proviso that one or more of the other elements in the precursor solid can be present in an oxidation state lower than its highest oxidation state, a, b, c, and d represent the molar ratio of the corresponding element to one mole of Mo.

In an embodiment the precursor solid comprises the empirical formula:

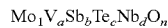

$$Mo_1V_aSb_bTe_cNb_dO_n$$

wherein a=0.21, $0 \leq b \leq 1.0$, $0 \leq c \leq 1.0$, d=0.09; b+c=0.24; n is the number of oxygen atoms required to satisfy valance requirements of all other elements present in the precursor solid with the proviso that one or more of the other elements in the precursor solid can be present in an oxidation state lower than its highest oxidation state, a, b, c, and d represent the molar ratio of the corresponding element to one mole of Mo.

The present invention provides a method for preparing a mixed oxide catalyst for use in producing acrylonitrile or methacrylonitrile from propane or isobutene by ammoxidation in a gaseous phase comprising the elements molybdenum (Mo), vanadium (V), niobium (Nb), oxygen (O) and at least one element selected from the group consisting of antimony (Sb) and tellurium (Te), further comprising heating precursor solid mixture, comprising compounds of molybdenum (Mo), vanadium (V) niobium (Nb), oxygen (O) and at least one element selected from the group consisting of antimony (Sb) and tellurium (Te), contacting with flowing gas at a first heating rate greater than about 15° C./min until the precursor solid mixture attains a temperature of not greater than 400° C., further contacting the precursor solid mixture with a hot zone temperature greater than about 100° C. The present invention provides an embodiment wherein the precursor solid mixture comprises contacting the flowing gas at a hot zone temperature greater than about 10° C., greater than about 200° C., greater than about 300° C., or greater than about 400° C. prior to the second heating rate step.

In one embodiment the precursor solid mixture is exposed to heating in the temperature range of 100-250° C. for not more than 7.5 min, 10 min, 15 min, or 30 min.

The precalcination temperature of the present invention comprises not greater than 400° C., 350° C., or 300° C.

The catalyst of the present invention may be used either supported or unsupported (i.e. the catalyst may comprise a support). Suitable supports are silica, alumina, zirconia, titania, or mixtures thereof. However, when zirconia or titania are used as support materials then the ratio of molybdenum to zirconium or titanium increases over the values shown in the above formulas, such that the Mo to Zr or Ti ratio is between about 1 to 10. A support typically serves as a binder for the catalyst resulting in a harder catalyst that is more attrition resistant. However, for commercial applications, an appropriate blend of both the active phase (i.e. the complex of catalytic oxides described above) and the support is helpful to obtain an acceptable activity and hardness (attrition resistance) for the catalyst. The support comprises between about 10 and 90 weight percent of the supported catalyst. Typically, the support comprises between about 40 and 60 weight percent of the supported catalyst. In one embodiment of this invention, the support may comprise as little as about 10 weight percent of the supported catalyst. In one embodiment of this invention, the support may comprise as little as about 30 weight percent of the supported catalyst. In another embodiment of this invention, the support may comprise as much as about 70 weight percent of the supported catalyst. Support materials are available which may contain one or more promoter elements, and such promoter elements may be incorporated into the catalyst via the support material.

The invention contemplates continuous processes for recovery and purification of organic values from hot gaseous mixtures which are obtained by catalytic ammoxidation of a light alkane hydrocarbon compounds. More particularly, this invention relates to recovery and refining of valuable nitrogen-containing organic compounds formed by catalytic oxidation of at least one feed compound selected from the group consisting of propane and isobutane in the presence of ammonia and oxygen to produce a gaseous reactor effluent containing the corresponding unsaturated mononitrile.

Propane is converted to acrylonitrile and isobutane to methacrylonitrile, by providing one or more of the aforementioned catalysts in a gas-phase flow reactor, and contacting the catalyst with propane or isobutane in the presence of oxygen (e.g. provided to the reaction zone in a feed stream comprising an oxygen-containing gas, such as air) and ammonia under reaction conditions effective to form acrylonitrile or methacrylonitrile. For this reaction, the feed stream comprises propane or isobutane, an oxygen-containing gas, such as air, and ammonia with the following molar ratios of: propane or isobutane to oxygen in a ratio ranging from about 0.125 to about 5, from about 0.25 to about 2.5, and propane or isobutane to ammonia in a ratio ranging from about 0.3 to about 2.5, from about 0.5 to about 2.0. The feed stream can also comprise one or more additional feed components, including acrylonitrile or methacrylonitrile product (e.g., from a recycle stream or from an earlier-stage of a multi-stage reactor), and steam. The feed stream can also comprise one or more additional feed components, including acrylonitrile or methacrylonitrile product (e.g., from a recycle stream or from an earlier-stage of a multi-stage reactor), or steam. For example, the feedstream can comprise about 5 percent to about 30 percent by weight relative to the total amount of the feed stream, or by mole relative to the amount of propane or isobutane in the feed stream. In one embodiment the catalyst compositions described herein are employed in the ammoxidation of propane to acrylonitrile in a once-through process, i.e., it operates without recycle of recovered but unreacted feed materials.

The specific design of the gas-phase flow reactor is not narrowly critical. Hence, the gas-phase flow reactor can be a fixed-bed reactor, a fluidized-bed reactor, or another type of reactor. The reactor can be a single reactor, or can be one reactor in a multi-stage reactor system. The reactor comprises one or more feed inlets for feeding a reactant feedstream to a reaction zone of the reactor, a reaction zone comprising the mixed metal oxide catalyst, and an outlet for discharging reaction products and unreacted reactants.

The reaction conditions are controlled to be effective for converting the propane to acrylonitrile, respectively, or the isobutane to methacrylonitrile. Generally, reaction conditions include a temperature ranging from about 300° C. to about 550° C., from about 325° C. to about 500° C., and in some embodiments from about 350° C. to about 450° C., and in other embodiments from about 430° C. to about 520° C. Generally, the flow rate of the propane or isobutene containing feedstream through the reaction zone of the gas-phase flow reactor can be controlled to provide a weight hourly space velocity (WHSV) ranging from about 0.02 to about 5, from about 0.05 to about 1, and in some embodiments from about 0.1 to about 0.5, in each case, for example, in grams propane or isobutane to grams of catalyst. The pressure of the reaction zone can be controlled to range from about 0 psig to about 200 psig, from about 0 psig to about 100 psig, and in some embodiments from about 0 psig to about 50 psig.

The resulting acrylonitrile or methacrylonitrile product can be isolated, if desired, from other side-products and from unreacted reactants according to methods known in the art. The resulting acrylonitrile or methacrylonitrile product can be isolated, if desired, from other side-products or from unreacted reactants according to methods known in the art.

The catalyst compositions described herein when employed in the single pass (i.e. no recycle) ammoxidation of propane are capable of producing a yield of about 57-58 percent acrylonitrile, with a selectivity of about 24% to $CO_x$ (carbon dioxide+carbon monoxide), and a selectivity of about 13% to a mixture of hydrogen cyanide (HCN) and acetonitrile or methyl cyanide ($CH_3CN$). The effluent of the reactor may also include unreacted oxygen ($O_2$), ammonia ($NH_3$) and entrained catalyst fines.

Processes for recovery and purification of the reaction products include quenching the gaseous reactor effluent with an aqueous quench liquid; forming an aqueous solution comprising the corresponding unsaturated mononitrile, hydrogen cyanide and other organic co-products; and using an integrated sequence of distillations and phase separations to recover for recycle of a useful aqueous liquid, and obtain valuable nitrogen-containing organic compounds and hydrogen cyanide products.

Propane, ammonia and oxygen mix together in the reactor and oxidation of propylene in the presence of ammonia takes place on the surface of the fluidized catalyst. A set of complex exothermic reactions takes place, thereby forming the following products: acrylonitrile, hydrogen cyanide, carbon dioxide, carbon monoxide, acetonitrile, acrolein, acrylic acid, water, other higher nitrites, aldehydes, ketones, acetic acid and a number of miscellaneous unknown organic compounds. Conversions of the three feeds generally are less than 100 percent, thus unreacted propane, ammonia, oxygen and nitrogen may be contained in the reactor effluent gas. Conversions of the three feeds generally are less than 100 percent, thus unreacted propane, ammonia, oxygen or nitrogen may be contained in the reactor effluent gas. The source of propane typically contains a small amount of propylene and some heavier hydrocarbon compounds most of which are purged from the process unreacted. A portion of the heat of the exothermic reaction is removed by sets of steam coils which generate and superheat waste steam at approximately 600 psig for process uses such as heat input for distillations in the products recovery and purification section of the process. Reactor effluent gas passes through cyclones, which remove catalyst fines from the gas. The gas is then further cooled in a reactor effluent cooler, which is comprised of a shell and tube exchanger using boiler feed-water as the cooling source.

As is well known in the art, performance of the oxidation catalysts is an important factor, perhaps the most significant factor, in the economics of this and other oxidation processes. Catalyst performance is measured by activity, i.e., conversion of reactants, selectivity, i.e. conversion of reactant to desired product, rate of production of desired product per unit of reactor volume per unit of time, and catalyst life, i.e. effective time on-stream before significant loss of activity or selectivity.

Factors upon which catalyst performance depends include composition, the methods of preparation, support, and calcination conditions. In addition to chemical performance requirements, other key properties include surface area, porosity, density, pore size distribution, hardness, strength, and resistance to mechanical attrition, particularly for fluid bed catalysts.

Typically, the ammoxidation process is carried out in a fluid-bed reactor. Where high alkane conversions are obtained, a single pass system comprises seconds of a residence time. Commercially recoverable quantities of acetonitrile and hydrocyanic acid are optional co-products. Approximately stoichometric quantities of propane, ammonia, and dioxygen are introduced into a fluidized bed of catalytic particles. Suitable operating conditions include pressures in a range from about 3 to about 35 psig (20.7 to 241.4 kPa gage), from about 5 to about 25 psig (34.5 to 172.4 kPa gage). Generally, temperatures are in a range from about 700° to 1000° F. (371° to 538° C.), in a range from about 750° to 950° F. (399° to 510° C.). Heat of reaction is removed by generation of steam to control the temperature and generating steam at temperatures of from about 300° to about 500° C. elevated pressure.

In order to illustrate the instant invention, samples of a catalyst, were prepared and then evaluated under similar reaction conditions. The compositions listed below are nominal compositions, based on the total metals added in the catalyst preparation. Since some metals may be lost or may not completely react during the catalyst preparation, the actual composition of the finished catalyst may vary slightly from the nominal compositions shown below.

Description of Catalyst Preparation:

Ammonium heptamolybdate, ammonium metavanadate and diantimony trioxide are added to water, followed by heating of the resultant mixture to temperatures of at least 50° C. and thereby obtain an aqueous mixture (A). In an embodiment heating is performed while stirring the mixture. Advantageously the aqueous mixture is heated to temperatures in the range upward from 70° C. to the normal boiling point of the mixture. The heating may be performed under reflux by using equipment having a reflux condenser. In the case of heating under reflux, the boiling point generally is in the range of from about 101° C. to 102° C. Elevated temperatures are maintained for 0.5 hour or more. When the heating temperature is low (e.g., lower than 50° C.), the heating time needs to be long. When the heating temperature is in a range of from 80° C. to 100° C., the heating time is typically in a range of from 1 to 5 hours.

Beneficially, after the heating, silica sol and hydrogen peroxide are added to the aqueous mixture (A). When hydrogen peroxide is added to the aqueous mixture (A), the amount of the hydrogen peroxide is such that the molar ratio of hydrogen peroxide to antimony ($H_2O_2$/Sb molar ratio) compound in terms of antimony is in the range of from 0.01 to 20, in the range of from 0.5 to 3, in the range of from 1 to 2.5. After addition of hydrogen peroxide, aqueous mixture (A) is stirred at temperatures in the range of from 30° C. to 70° C. for from 30 minutes to 2 hours.

An aqueous liquid (B) is obtained by adding a niobium compound (e.g., niobic acid) to water, followed by heating of the resultant mixture to temperatures in a range of from 50° C. up to nearly 100° C. Advantageously aqueous liquid (B) contains a dicarboxylic acid (e.g., oxalic acid) in addition to the niobium compound. Generally, the molar ratio of the dicarboxylic acid to the niobium compound in terms of niobium is in the range of from 1 to 4, advantageously in the range of from 2 to 4. That is, in this case, niobic acid and oxalic acid are added to water, followed by heating and stirring of the resultant mixture to thereby obtain an aqueous liquid (B).

A useful method for preparing the above-mentioned aqueous liquid (B), comprises the following steps: (1) mixing water, a dicarboxylic acid (e.g. oxalic acid) and a niobium compound (e.g. niobic acid) thereby obtaining a preliminary niobium-containing aqueous solution or a niobium-containing aqueous mixture having suspended therein a part of the niobium compound; (2) cooling the preliminary niobium-containing aqueous solution or niobium-containing aqueous mixture thereby precipitating a part of the dicarboxylic acid; and (3) removing the precipitated dicarboxylic acid from the preliminary niobium-containing aqueous solution, or removing the precipitated dicarboxylic acid and the suspended niobium compound from the niobium-containing aqueous mixture, thereby obtaining a niobium-containing aqueous liquid (B). Aqueous liquids (B) obtained in the above method usually have a dicarboxylic acid/niobium molar ratio within the range of from about 2 to 4.

A particularly useful dicarboxylic acid is oxalic acid, and useful niobium compounds in step (1) of this method include niobic acid, niobium hydrogenoxalate and ammonium niobium oxalate. These niobium compounds can be used in the form of a solid, a mixture, or a dispersion in an appropriate medium. When either niobium hydrogenoxalate or ammonium niobium oxalate is used as the niobium compound, the dicarboxylic acid may not be used. When niobic acid is used as the niobium compound, in order to remove acidic impurities with which the niobic acid may have been contaminated during the production thereof, the niobic acid may be washed with an aqueous ammonia solution and/or water prior to use. In an embodiment, freshly prepared niobium compound can be used as the niobium compound. However, in the above-mentioned method, a niobium compound can be used which is slightly denatured (for example by dehydration) as a result of a long-term storage and the like. In step (1) of this method, the dissolution of the niobium compound can be promoted by the addition of a small amount of aqueous ammonia or by heating.

The concentration of the niobium compound (in terms of niobium) in the preliminary niobium-containing aqueous solution or aqueous mixture can be maintained within the range of from 0.2 to 0.8 mol/kg of the solution or mixture. In an embodiment, dicarboxylic acid can be used in an amount such that the molar ratio of dicarboxylic acid to niobium compound in terms of niobium is approximately 3 to 6. When an excess amount of the dicarboxylic acid is used, a large amount of the niobium compound can be dissolved in the aqueous solution of dicarboxylic acid; however, a disadvantage is likely to arise in that the amount of the dicarboxylic acid which is caused to precipitate by cooling the obtained preliminary niobium-containing aqueous solution or mixture becomes too large, thus decreasing the utilization of the dicarboxylic acid. On the other hand, when an unsatisfactory amount of the dicarboxylic acid is used, a disadvantage is likely to arise in that a large amount of the niobium compound remains undissolved and is suspended in the aqueous solution of the dicarboxylic acid to form a mixture, wherein the suspended niobium compound is removed from the aqueous mixture, thus decreasing the degree of utilization of the niobium compound.

Any suitable method of cooling may be used in step (2). For example, the cooling can be performed simply by means of an ice bath.

The removal of the precipitated dicarboxylic acid (or precipitated dicarboxylic acid and the dispersed niobium compound) in step (3) can be easily performed by conventional methods, for example, by decantation or filtration.

When the dicarboxylic acid/niobium molar ratio of the obtained niobium-containing aqueous solution is outside the range of from about 2 to 4, either the niobium compound or dicarboxylic acid may be added to the aqueous liquid (B) so that the dicarboxylic acid/niobium molar ratio of the solution falls within the above-mentioned range. However, in general, such an operation is unnecessary since an aqueous liquid (B) having the dicarboxylic acid/niobium molar ratio within the range of from 2 to 4 can be prepared by appropriately controlling the concentration of the niobium compound, the ratio of the dicarboxylic acid to the niobium compound and the cooling temperature of the above-mentioned preliminary niobium-containing aqueous solution or aqueous mixture.

The aqueous liquid (B) may also be prepared comprising further component(s). For example, at least a part of the aqueous liquid (B) containing a niobium compound or containing a mixture of a niobium compound and a dicarboxylic acid is used together with hydrogen peroxide. In this case, it is beneficial that the amount of hydrogen peroxide provided a molar ratio of hydrogen peroxide to niobium compound ($H_2O_2$/Nb molar ratio) in terms of niobium is in the range of from 0.5 to 20, from 1 to 20.

In another example, at least part of the aqueous liquid (B), containing a niobium compound or containing a mixture of a niobium compound and a dicarboxylic acid, or a mixture thereof with hydrogen peroxide, further comprises an antimony compound (e.g. diantimony trioxide), a titanium compound (e.g. titanium dioxide, which can be a mixture of rutile and anatase forms) and/or a cerium compound (e.g. cerium acetate). In this case, the amount of the hydrogen peroxide is such that the molar ratio of hydrogen peroxide to niobium compound ($H_2O_2$/Nb molar ratio) in terms of niobium is in the range of from 0.5 to 20, from 1 to 20. In another example, the antimony compound mixed with at least a part of the aqueous liquid (B) and the hydrogen peroxide is such that the molar ratio (Sb/Nb molar ratio) of the antimony compound in terms of antimony to the niobium compound in terms of niobium is not more than 5, in the range of from 0.01 to 2.

Aqueous mixture (A) and aqueous liquid (B) are mixed together in an appropriate ratio in accordance with the desired composition of the catalyst, to thereby provide an aqueous mixture of ingredients, typically, in the form of a slurry. The content of ingredients in the aqueous mixture is generally in a range upward from about 50 percent by weight, from 70 to 95 percent by weight, from 75 to 90 percent by weight.

In the case of producing a silica carrier-supported catalyst of the present invention, the aqueous raw material mixture is prepared so as to contain a source of silica (namely, a silica sol or fumed silica). The amount of the source of silica can be appropriately adjusted in accordance with the amount of the silica carrier in the catalyst to be obtained.

Drying Step

The aqueous mixture of ingredients is dried to thereby provide a dry catalyst precursor. Drying may be conducted by conventional methods, such as spray drying or evaporation drying. Spray drying is particularly useful, because a fine, spherical, dry catalyst precursor is obtained. The spray drying can be conducted by centrifugation, by the two-phase flow nozzle method or by the high-pressure nozzle method. As a heat source for drying, it is an embodiment to use air which has been heated by steam, an electric heater and the like. It is an embodiment that the temperature of the spray dryer at an entrance to the dryer section thereof is from 150° C. to 300° C.

Calcination Step

In the calcination step, the dry catalyst precursor is converted into a mixed metal oxide catalyst. Calcinations can be conducted using a rotary kiln, a fluidized-bed kiln, fludized bed reactor, fixed bed reactor, or the like. Conditions of calcination are preselected such that the catalyst formed has a specific surface area of from about 5 $m^2/g$ to about 35 $m^2/g$, from about 15 $m^2/g$ to about 20 $m^2/g$.

Calcination involves heating the dry catalyst precursor up to a final temperature in the range of about 600-680° C.

In the present invention, calcination process comprises heating of the dry catalyst precursor continuously or intermittently to elevate from a temperature which is less than 200° C. to a precalcination temperature of not greater than about 400° C., not greater than about 350° C., not greater than about 300° C. at a rate of greater than 15° C./min. In an embodiment, the precalcination temperature is 300° C. In an embodiment the heating rate is about 20° C./min. In another embodiment, the heating rate is 25° C./min. In another embodiment, the heating rate is 30° C./min. Yet in another embodiment, the dry catalyst precursor is introduced into a hot calciner maintained at about 300° C. or slightly higher in order to allow the temperature of the precursor to quickly increase to about 300° C.

The heating rate from the precalcination temperature to the final temperature can be about 0.5° C./min, 1° C./min, 2° C./min or 5° C./min or any rate in the range of 0.5-5° C./min. In one embodiment, the heating rate for the temperature range of about 300° C. to the intermediate temperature is about 1° C./min and from the intermediate temperature to the final temperature, the heating rate is greater than 15° C./min, or greater than or equal to 20° C./min, or greater than or equal to 25° C./min, or greater than or equal to 30° C./min. In another embodiment, the solid can be cooled after attaining the intermediate temperature and then heated to the final temperature at a heating rate of greater than about 15° C./min, or greater than or equal to 20° C./min, or greater than or equal to 25° C./min, or greater than or equal to 30° C./min.

In an embodiment of the invention, the calcination is done in two calcination stages: (1) up to intermediate or precalcination temperature and (2) from intermediate or precalcination to final temperature. In one embodiment the solid from the stage (1) calcination, optionally cooled, is introduced into a hot calciner maintained at a temperature equal to about the final temperature in order to allow the temperature of the precursor to quickly increase to the final temperature.

In one embodiment, the heating rate for the temperature range of about 300° C. to about 340-350° C., 345° C. is about 0.5° C./min or 1° C./min or about 2° C./min or about 5° C./min or any rate in the range of 0.5 to 5° C./min. In one embodiment, the solid is held at a temperature in the range of 300-400° C., in the range of 340-350° C., at 345° C. for a period of about 1 to 4 hours. In one embodiment, the solid is heated at a rate of 2.45° C./min in the temperature range of 345-680° C.

Upon attaining the final temperature, the solid can be held at that temperature for a period of from about 1 hour to about 3 hours, about 2 hours.

The final temperature can be 600° C., 610° C., 620° C., 630° C., 640° C., 650° C., 660° C., 670° C., and 680° C. or any temperature in the 600-680° C. range. In one embodiment, the solid is heated at rate a rate of 0.5° C./min from about 600° C. to about 680° C. In one embodiment, the solid is heated at rate a rate of 1° C./min from about 600° C. to about 680° C.

The calcination can be conducted in air or under a flow of air. However, at least a part of the calcination is conducted in an atmosphere of a gas (e.g., under a flow of a gas), such as nitrogen gas that is substantially free of oxygen. The present invention contemplates using inert gas. The inert gas can comprise a noble gas. The gas can comprise nitrogen. The gas can comprise selection from air, steam, super heated steam, carbon monoxide, and carbon dioxide. In one embodiment of the present invention the calcination can be carried out under a flow of nitrogen gas that is substantially free of oxygen for both the temperature ranges of (1) up to about 400-450° C. and (2) above about 400-450° C. In another embodiment of the present invention the calcination can be carried out under a flow of air for the temperature range of (1) up to about 400-450° C. and under a flow of nitrogen gas that is substantially free of oxygen for the temperature range of (2) above about 400-450° C. The flow rate of gas can be critical especially for the temperature range of (1) up to about 400-450° C. The flow rate of gas can be in the range of about 0.67 to about 2.5 sccm per g catalyst precursor per minute.

Catalyst Testing

Fixed Bed Testing: Catalyst was evaluated in a laboratory fixed bed reactor having a diameter of about 4.5 mm (about 3/16 inch). The reactor was charged with about 0.3 to 0.5 g of particulate catalyst. Propane was fed into the reactor at a rate of about 0.05 to 0.15 WWH (i.e., weight of propane/weight of catalyst/hour). Ammonia was fed into the reactor at a flow rate such that ammonia to propane ratio was in the range for about 1 to 1.5. Pressure inside the reactor was maintained at about 2 to 15 psig. Reaction temperatures were in the range of about 420 to 460° C.

Fluid Bed Testing: Catalyst was evaluated in a laboratory 40 cc fluid bed reactor having a diameter of 1-inch. The reactor was charged with about 20 to about 45 g of particulate catalyst or catalyst mixture. Propane was fed into the reactor at a rate of about 0.04 to about 0.15 WWH (i.e., weight of propane/weight of catalyst/hour). Pressure inside the reactor was maintained at about 2 to about 15 psig. Reaction temperatures were in the range of about 420 to about 460° C. Generally, ammonia was fed into the reactor at a flow rate such that ammonia to propane ratio was from about 1 to about 1.5. Oxygen was fed into the reactor at a flow rate such that oxygen to propane ratio was about 3.4. Nitrogen was fed into the reactor at a flow rate such that nitrogen to propane ratio was about 12.6.

As used herein, the term "about" modifying any amount refers to the variation in that amount encountered in real world conditions of producing catalyst or producing catalyst precursors, e.g., in the lab, pilot plant, or production facility. For example, an amount of an ingredient employed in a mixture when modified by "about" includes the variation and degree of care typically employed in measuring in a catalyst or catalyst precursor production plant or lab. For example, the amount of a component of a product when modified by "about" includes the variation between batches in catalyst or catalyst precursors production plant or lab and the variation inherent in the analytical method. Whether or not modified by "about," the amounts include equivalents to those amounts. Any quantity stated herein and modified by "about" can also be employed in the present invention as the amount not modified by "about."

EXAMPLES OF THE INVENTION

The following examples will serve to illustrate certain specific embodiments of the inventions herein disclosed. These examples should not, however, be construed as limiting the scope of the novel invention as there are many variations which may be made thereon without departing from the spirit of the disclosed invention, as those of skill in the art will recognize.

A solid precursor to a mixed metal oxide catalyst wherein the precursor solid comprises the empirical formula:

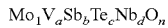

$Mo_1V_aSb_bTe_cNb_dO_n$ wherein a=0.21, 0≦b≦1.0, 0≦c≦1.0, d=0.09; b+c=0.24; n is the number of oxygen atoms required to satisfy valance requirements of all other elements present in the precursor solid with the proviso that one or more of the other elements in the precursor solid can be present in an oxidation state lower than its highest oxidation state, a, b, c, and d represent the molar ratio of the corresponding element to one mole of Mo; was prepared by a method disclosed in the description section and portions of this catalyst precursors were calcined using different calcination conditions as described in the examples that follow.

Comparative Example

About 60 g of the solid precursor was calcined under flow of nitrogen at the rate of 100 sccm in a 1-foot vertical tube as follows. The temperature of the loaded vertical tube was raised at the rate of about 1.35° C./min, to 345° C., the temperature was maintained at 345° C. for 4 hours. In the next step the temperature was again raised at the rate of about 2.45° C./min to a temperature of 640° C. This calcination was completed by maintaining temperature at 640° C. for 2 hours. This catalyst was evaluated in a laboratory fixed bed reactor that gave an acrylonitrile yield of 35.5% at a temperature of 415° C. at ambient pressure and 0.05 WWH. The acrylonitrile yield was 36.0% at a temperature of 425° C. at ambient pressure and 0.07 WWH.

Example 1

About 60 g of the solid precursor was calcined under flow of nitrogen at the rate of 100 sccm in a 1-foot vertical tube as follows. The temperature of the loaded vertical tube was raised at the rate of about 20° C./min, to 300° C., then at the rate of 0.5° C./min, to 345° C. The temperature was maintained at 345° C. for 4 hours. In the next step the temperature was again raised at the rate of about 2.45° C./min to a temperature of 640° C. This calcination was completed by maintaining temperature at 640° C. for 2 hours. This catalyst was evaluated in a laboratory fixed bed reactor that gave an acrylonitrile yield of 35.7% at a temperature of 415° C. at ambient pressure and 0.05 WWH.

Example 2

About 60 g of the solid precursor was calcined under flow of nitrogen at the rate of 100 sccm in a 1-foot vertical tube as follows. The temperature of the loaded vertical tube was raised at the rate of about 20° C./min, to 300° C., then at the rate of 1° C./min, to 345° C. The temperature was maintained at 345° C. for 4 hours. In the next step the temperature was again raised at the rate of about 2.45° C./min to a temperature of 640° C. This calcination was completed by maintaining temperature at 640° C. for 2 hours. This catalyst was evaluated in a laboratory fixed bed reactor that gave an acrylonitrile yield of 36.2% at a temperature of 415° C. at ambient pressure and 0.05 WWH.

Example 3

About 60 g of the solid precursor was calcined under flow of nitrogen at the rate of 100 sccm in a 1-foot vertical tube as follows. The temperature of the loaded vertical tube was raised at the rate of about 20° C./min, to 300° C., then at the rate of 2° C./min, to 345° C. The temperature was maintained at 345° C. for 4 hours. In the next step the temperature was again raised at the rate of about 2.45° C./min to a temperature of 640° C. This calcination was completed by maintaining temperature at 640° C. for 2 hours. This catalyst was evaluated in a laboratory fixed bed reactor that gave an acrylonitrile yield of 38.3% at a temperature of 415° C. at ambient pressure and 0.05 WWH.

Example 4

About 60 g of the solid precursor was calcined under flow of nitrogen at the rate of 100 sccm in a 1-foot vertical tube as follows. The temperature of the loaded vertical tube was raised at the rate of about 20° C./min, to 300° C., then at the rate of 5° C./min, to 345° C. The temperature was maintained at 345° C. for 4 hours. In the next step the temperature was again raised at the rate of about 2.45° C./min to a temperature of 640° C. This calcination was completed by maintaining temperature at 640° C. for 2 hours. This catalyst was evaluated in a laboratory fixed bed reactor that gave an acrylonitrile yield of 40.7% at a temperature of 415° C. at ambient pressure and 0.05 WWH.

Example 5

About 60 g of the solid precursor was calcined under flow of nitrogen at the rate of 100 sccm in a 1-foot vertical tube as follows. The temperature of the loaded vertical tube was raised at the rate of about 20° C./min, to 300° C., then at the rate of 0.5° C./min, to a temperature of 640° C. This calcination was completed by maintaining temperature at 640° C. for 2 hours. This catalyst was evaluated in a laboratory fixed bed reactor that gave an acrylonitrile yield of 42.1% at a temperature of 425° C. at ambient pressure and 0.07 WWH.

Example 6

About 60 g of the solid precursor was calcined under flow of nitrogen at the rate of 100 sccm in a 1-foot vertical tube as follows. The temperature of the loaded vertical tube was raised at the rate of about 20° C./min, to 300° C., then at the rate of 1° C./min, to a temperature of 640° C. This calcination was completed by maintaining temperature at 640° C. for 2 hours. This catalyst was evaluated in a laboratory fixed bed reactor that gave an acrylonitrile yield of 44.1% at a temperature of 425° C. at ambient pressure and 0.07 WWH.

Example 7

About 60 g of the solid precursor was calcined under flow of nitrogen at the rate of 100 sccm in a 1-foot vertical tube as follows. The temperature of the loaded vertical tube was raised at the rate of about 20° C./min, to 300° C., then at the rate of 2° C./min, to a temperature of 640° C. This calcination was completed by maintaining temperature at 640° C. for 2 hours. This catalyst was evaluated in a laboratory fixed bed reactor that gave an acrylonitrile yield of 38.4% at a temperature of 425° C. at ambient pressure and 0.07 WWH.

Example 8

About 60 g of the solid precursor was calcined under flow of nitrogen at the rate of 100 sccm in a 1-foot vertical tube as follows. The temperature of the loaded vertical tube was raised at the rate of about 20° C./min, to 300° C., then at the rate of 5° C./min, to a temperature of 640° C. This calcination was completed by maintaining temperature at 640° C. for 2 hours. This catalyst was evaluated in a laboratory fixed bed reactor that gave an acrylonitrile yield of 36.8% at a temperature of 425° C. at ambient pressure and 0.07 WWH.

Example 9

About 60 g of the solid precursor was calcined under flow of nitrogen at the rate of 100 sccm in a 1-foot vertical tube as follows. The temperature of the loaded vertical tube was raised at the rate of about 1° C./min, to a temperature of 640° C. This calcination was completed by maintaining temperature at 640° C. for 2 hours. This catalyst was evaluated in a laboratory fixed bed reactor that gave an acrylonitrile yield of 29.6% at a temperature of 425° C. at ambient pressure and 0.07 WWH.

Example 10

About 60 g of the solid precursor was calcined under flow of nitrogen at the rate of 100 sccm in a 1-foot vertical tube as follows. The temperature of the loaded vertical tube was raised at the rate of about 2° C./min, to a temperature of 640° C. This calcination was completed by maintaining temperature at 640° C. for 2 hours. This catalyst was evaluated in a laboratory fixed bed reactor that gave an acrylonitrile yield of 29.2% at a temperature of 425° C. at ambient pressure and 0.07 WWH.

Example 11

About 60 g of the solid precursor was calcined under flow of nitrogen at the rate of 100 sccm in a 1-foot vertical tube as follows. The temperature of the loaded vertical tube was raised at the rate of about 5° C./min, to a temperature of 640° C. This calcination was completed by maintaining temperature at 640° C. for 2 hours. This catalyst was evaluated in a laboratory fixed bed reactor that gave an acrylonitrile yield of 26.5% at a temperature of 425° C. at ambient pressure and 0.07 WWH.

Example 12

About 60 g of the solid precursor was calcined under flow of nitrogen at the rate of 100 sccm in a 1-foot vertical tube as follows. The temperature of the loaded vertical tube was raised at the rate of about 20° C./min, to 300° C., then at the rate of 1° C./min, to a temperature of 630° C. This calcination was completed by maintaining temperature at 630° C. for 2 hours. This catalyst was evaluated in a laboratory fluid bed reactor wherein the catalyst was mixed with 0.04 g $Sb_2O_3$ powder per g catalyst that gave an acrylonitrile yield of 40.0% at a temperature of 440° C. at 10 psig pressure and 0.06 WWH.

Example 13

About 60 g of the solid precursor was calcined under flow of nitrogen at the rate of 80 sccm in a 1-foot vertical tube as follows. The temperature of the loaded vertical tube was raised at the rate of about 20° C./min, to 300° C., then at the rate of 1° C./min, to a temperature of 630° C. This calcination was completed by maintaining temperature at 630° C. for 2 hours. This catalyst was evaluated in a laboratory fluid bed reactor wherein the catalyst was mixed with 0.04 g $Sb_2O_3$ powder per g catalyst that gave an acrylonitrile yield of 39.5% at a temperature of 440° C. at 10 psig pressure and 0.06 WWH.

Example 14

About 60 g of the solid precursor was calcined under flow of nitrogen at the rate of 60 sccm in a 1-foot vertical tube as follows. The temperature of the loaded vertical tube was raised at the rate of about 20° C./min, to 300° C., then at the rate of 1° C./min, to a temperature of 630° C. This calcination was completed by maintaining temperature at 630° C. for 2 hours. This catalyst was evaluated in a laboratory fluid bed reactor wherein the catalyst was mixed with 0.04 g $Sb_2O_3$ powder per gram catalyst that gave an acrylonitrile yield of 33.8% at a temperature of 440° C. at 10 psig pressure and 0.06 WWH.

Example 15

About 60 g of the solid precursor was calcined under flow of nitrogen at the rate of 40 sccm in a 1-foot vertical tube as follows. The temperature of the loaded vertical tube was raised at the rate of about 20° C./min, to 300° C., then at the rate of 1° C./min, to a temperature of 630° C. This calcination was completed by maintaining temperature at 630° C. for 2 hours. This catalyst was evaluated in a laboratory fluid bed reactor wherein the catalyst was mixed with 0.04 g $Sb_2O_3$ powder per gram catalyst that gave an acrylonitrile yield of 31.1% at a temperature of 440° C. at 10 psig pressure and 0.06 WWH.

TABLE 1

| Example | $N_2$ Flow cm³/g/min | Heating Rate, ° C./min To 300° C. | Heating Rate, ° C./min 300-345° C. | Heating Rate, ° C./min 345-640° C. | Hold Time, min At 345° C. | Hold Time, min At 640° C. | AN Yield,* % 0.05 WWH, 415° C. | AN Yield,* % 0.07 WWH, 425° C. |
|---|---|---|---|---|---|---|---|---|
| Comp. | 1.67 | | 1.35 | 2.45 | 240 | 120 | 35.5 | 36.0 |
| 1 | 1.67 | 20 | 0.5 | 2.45 | 240 | 120 | 35.7 | — |
| 2 | 1.67 | 20 | 1 | 2.45 | 240 | 120 | 36.2 | — |
| 3 | 1.67 | 20 | 2 | 2.45 | 240 | 120 | 38.3 | — |
| 4 | 1.67 | 20 | 5 | 2.45 | 240 | 120 | 40.7 | — |
| 5 | 1.67 | 20 | 0.5 | | | 0 | 120 | — | 42.1 |
| 6 | 1.67 | 20 | 1 | | 0 | 120 | — | 44.1 |
| 7 | 1.67 | 20 | 2 | | 0 | 120 | — | 38.4 |
| 8 | 1.67 | 20 | 5 | | 0 | 120 | — | 36.8 |
| 9 | 1.67 | | 1 | | 0 | 120 | — | 29.6 |
| 10 | 1.67 | | 2 | | 0 | 120 | — | 29.2 |
| 11 | 1.67 | | 5 | | 0 | 120 | — | 26.5 |

*Fixed Bed Reactor Test

TABLE 2

| Example | Gas Flow Rate, cm³/g/min | Heating Rate To 300° C., ° C./min | Heating Rate: 300-630° C., ° C./min | Hold Time at 630° C., min | AN Yield,** 0.06 WWH, 440° C., % |
|---|---|---|---|---|---|
| 12 | 1.67 | 20 | 1 | 120 | 40.0 |
| 13 | 1.33 | 20 | 1 | 120 | 39.5 |
| 14 | 1.00 | 20 | 1 | 120 | 33.8 |
| 15 | 0.67 | 20 | 1 | 120 | 31.1 |

**Fluid Bed Reactor Test follows. The temperature of the loaded vertical tube was raised at the rate of about 20° C./min, to 300° C., then at the rate of 1° C./min, to a temperature of 630° C. This calcination was completed by maintaining temperature at 630° C. for 2 hours. This catalyst was evaluated in a laboratory fluid bed reactor wherein the catalyst was mixed with 0.04 g $Sb_2O_3$

What is claimed is:

1. A method for preparing a mixed oxide catalyst for use in producing acrylonitrile or methacrylonitrile from propane or isobutene by ammoxidation in a gaseous phase comprising the elements molybdenum (Mo), vanadium (V), niobium (Nb), oxygen (O) and at least one element selected from the group consisting of antimony (Sb) and tellurium (Te), said method comprising heating a precursor solid mixture of said mixed oxide catalyst comprising compounds of molybdenum (Mo), vanadium (V) niobium (Nb), oxygen (O) and at least one element selected from the group consisting of antimony (Sb) and tellurium (Te), in contact with flowing gas, at a first heating rate greater than about 15° C./min until the precursor solid mixture attains a precalcination temperature of not greater than 400° C.

2. The method according to claim 1 wherein the method further comprises heating said precursor solid mixture at a second heating rate of greater than about 0.5° C./min until the precursor solid mixture attains a temperature of about 590-680° C.

3. The method according to claim 2 wherein the method comprises a second heating rate greater than about 1° C./min.

4. The method according to claim 2 wherein the method comprises a second heating rate greater than about 2° C./min.

5. The method according to claim 2 wherein the method comprises a second heating rate greater than about 5° C./min.

6. The method according to claim 2 wherein the second heating rate is performed in an atmosphere substantially free of oxygen.

7. The method according to claim 2 wherein the method further comprises holding the precursor solid mixture at a temperature of about 590-680° C. for about two (2) hours.

8. The method according to claim 1 wherein the mixed oxide catalyst comprises the elements molybdenum (Mo), vanadium (V), niobium (Nb), and antimony (Sb).

9. The method according to claim 1 wherein the mixed oxide catalyst comprises the elements molybdenum (Mo), vanadium (V), niobium (Nb), and tellurium (Te).

10. The method according to claim 1 wherein the mixed oxide catalyst comprises the elements molybdenum (Mo), vanadium (V), niobium (Nb), antimony (Sb), and tellurium (Te).

11. The method according to claim 1 wherein the precursor solid mixture comprises the elements molybdenum (Mo), vanadium (V), niobium (Nb), antimony (Sb), and oxygen (O).

12. The method according to claim 1 wherein the precursor solid mixture comprises the elements molybdenum (Mo), vanadium (V), niobium (Nb), tellurium (Te), and oxygen (O).

13. The method according to claim 1 wherein the precursor solid mixture comprises the elements molybdenum (Mo), vanadium (V), niobium (Nb), antimony (Sb), tellurium (Te), and oxygen (O).

14. The method according to claim 1 wherein the gas comprises inert gas.

15. The method according to claim 14 wherein the inert gas comprises noble gas.

16. The method of claim 1 wherein the gas comprises nitrogen.

17. The method according to claim 1 wherein the gas comprises selection from air, steam, super heated steam, and carbon dioxide.

18. The method according to claim 1 wherein the method comprises a first heating rate greater than about 20° C./min.

19. The method according to claim 1 wherein the precursor solid comprises the empirical formula:

$$Mo_1V_aSb_bTe_cNb_dO_n$$

wherein $0.1 \leq a \leq 1.0$, $0 \leq b \leq 1.0$, $0 \leq c \leq 1.0$, $0.001 \leq d \leq 0.25$; n is the number of oxygen atoms required to satisfy valance requirements of all other elements present in the precursor solid with the proviso that one or more of the other elements in the precursor solid can be present in an oxidation state lower than its highest oxidation state, a, b, c, and d represent the molar ratio of the corresponding element to one mole of Mo.

20. The method according to claim 1 wherein the precursor solid comprises the empirical formula:

$$Mo_1V_aSb_bTe_cNb_dO_n$$

wherein $a=0.21$, $0 \leq b \leq 1.0$, $0 \leq c \leq 1.0$, $d=0.09$; $b+c=0.24$; n is the number of oxygen atoms required to satisfy valance requirements of all other elements present in the precursor solid with the proviso that one or more of the other elements in the precursor solid can be present in an oxidation state lower than its highest oxidation state, a, b, c, and d represent the molar ratio of the corresponding element to one mole of Mo.

21. A method for preparing a mixed oxide catalyst for use in producing acrylonitrile or methacrylonitrile from propane or isobutene by ammoxidation in a gaseous phase comprising the elements molybdenum (Mo), vanadium (V), niobium (Nb), oxygen (O) and at least one element selected from the group consisting of antimony (Sb) and tellurium (Te), said method comprising heating a precursor solid mixture, comprising compounds of molybdenum (Mo), vanadium (V) niobium (Nb), oxygen (O) and at least one element selected from the group consisting of antimony (Sb) and tellurium (Te), in contact with flowing gas, at a first heating rate greater than about 15° C./min until the precursor solid mixture attains a temperature of not greater than 400° C., further contacting the precursor solid mixture with a hot zone temperature greater than about 100° C.

22. The method according to claim 21 wherein the method comprises a hot zone temperature greater than about 200° C.

23. The method according to claim 22 wherein the method comprises a hot zone temperature greater than about 300° C.

24. The method according to claim 1 wherein the precalcination temperature is not greater than about 350° C.

25. The method according to claim 1 wherein the precalcination temperature is not greater than about 300° C.

* * * * *